United States Patent
Sprung

(10) Patent No.: US 8,845,532 B2
(45) Date of Patent: Sep. 30, 2014

(54) METHOD FOR MONITORING A PERSON BEING EXAMINED

(75) Inventor: Katrin Christel Sprung, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 1236 days.

(21) Appl. No.: 12/315,317

(22) Filed: Dec. 2, 2008

(65) Prior Publication Data

US 2009/0149720 A1 Jun. 11, 2009

(30) Foreign Application Priority Data

Dec. 6, 2007 (DE) .......................... 10 2007 058 684

(51) Int. Cl.
| | | |
|---|---|---|
| A61B 5/00 | (2006.01) | |
| G01R 33/28 | (2006.01) | |
| A61B 6/04 | (2006.01) | |
| A61B 5/055 | (2006.01) | |
| A61B 6/00 | (2006.01) | |
| A61B 5/11 | (2006.01) | |

(52) U.S. Cl.
CPC ............ *A61B 5/0555* (2013.01); *G01R 33/283* (2013.01); *G01R 33/28* (2013.01); *A61B 5/6892* (2013.01); *A61B 6/04* (2013.01); *A61B 5/7207* (2013.01); *A61B 5/11* (2013.01); *A61B 5/721* (2013.01); *A61B 6/527* (2013.01); *A61B 6/0407* (2013.01); *A61B 5/704* (2013.01)
USPC ....................................................... 600/301

(58) Field of Classification Search
None
See application file for complete search history.

(56) References Cited

U.S. PATENT DOCUMENTS

| | | | | |
|---|---|---|---|---|
| 4,175,263 | A  * | 11/1979 | Triplett et al. ............. | 340/573.4 |
| 6,208,250 | B1 * | 3/2001 | Dixon et al. ............... | 340/573.1 |
| 6,719,708 | B1 | 4/2004 | Jansen | |
| 7,505,803 | B2 | 3/2009 | Boese et al. | |
| 7,942,824 | B1 * | 5/2011 | Kayyali et al. ................ | 600/538 |
| 2005/0065447 | A1 * | 3/2005 | Lee et al. ........................ | 600/529 |
| 2005/0113670 | A1 * | 5/2005 | Salla et al. ..................... | 600/413 |
| 2005/0113671 | A1 * | 5/2005 | Salla et al. ..................... | 600/413 |
| 2005/0113673 | A1 * | 5/2005 | Avinash et al. ................ | 600/413 |
| 2006/0173273 | A1 * | 8/2006 | Boese et al. ................... | 600/407 |
| 2007/0225574 | A1 * | 9/2007 | Ueda .............................. | 600/300 |
| 2008/0064968 | A1 * | 3/2008 | Martin et al. .................. | 600/493 |
| 2008/0076995 | A1 * | 3/2008 | Hoarau .......................... | 600/344 |
| 2008/0228084 | A1 * | 9/2008 | Bedard et al. .................. | 600/477 |
| 2008/0275314 | A1 * | 11/2008 | Mack et al. .................... | 600/301 |
| 2009/0149768 | A1 * | 6/2009 | Sprung .......................... | 600/523 |

FOREIGN PATENT DOCUMENTS

| | | |
|---|---|---|
| DE | 10001698 A1 | 4/2001 |
| DE | 102005004142 A1 | 8/2006 |

* cited by examiner

*Primary Examiner* — William Thomson
*Assistant Examiner* — Bobby Soriano

(57) ABSTRACT

The invention relates to a method for monitoring recording of measurement data of a person being examined who is positioned on a couch in medical diagnostic equipment, comprising the following steps, recording the measurement data to create image data; detecting the pressure characteristic that is exerted on the couch by the person being examined; automatic analysis of the pressure characteristic by comparing the detected characteristic with a predetermined pressure characteristic; and informing an operator of the medical diagnostic equipment if the analyzed pressure characteristic does not match the predetermined pressure characteristic.

17 Claims, 3 Drawing Sheets

METHOD FOR MONITORING A PERSON BEING EXAMINED

CROSS REFERENCE TO RELATED APPLICATIONS

This application claims the benefits of German application No. 10 2007 058 684.3 filed Dec. 6, 2007 and is incorporated by reference herein in its entirety.

FIELD OF INVENTION

The present invention relates to a method for monitoring recording of measurement data of a person being examined who is positioned on a couch in medical diagnostic equipment, and to the medical diagnostic equipment itself. The invention is used in particular, but not exclusively, in magnetic resonance systems in which the person being examined is moved into the magnets on a couch in order to create image data or MR images of the person being examined.

BACKGROUND OF THE INVENTION

The cooperation of the person being examined is very important when generating MR image data. In addition to a large number of important measuring parameters and the fact that in some measurements it may be important that the person being examined holds his breath or that the measurement is coordinated with the cardiac cycle, it is also very important that the person being examined does not move for the duration of the examination, even if no measurement is currently taking place. The unvarying position of the person being examined, in addition to optimum parameter definition in the imaging sequence, is crucial to the resulting image quality. Once measurement is complete it can sometimes be difficult to determine the cause of poor image quality. If the image quality of the recorded image data is not satisfactory, a measurement has to be repeated, whereby the magnetic resonance system is blocked for longer than necessary by a person being examined, and this increases the cost of an MR examination unnecessarily.

In the prior art it is known to carry out camera-assisted monitoring of the person being examined via a separate monitor. However for this it is necessary for the person being examined to be observed throughout the entire examination in order to detect movements. In practice however it is often the case that for operation of the MR system or medical diagnostic equipment, an operator is already making adjustments for the subsequent measurements or is occupied with other tasks and consequently does not have the monitors constantly in view. If the person being examined moves, this can be overlooked and leads to poor image quality. The case can also occur where images of different layer orientations no longer spatially match up as a result of the movement because, following the movement, the person being examined is often not lying in exactly the same position as before the movement. Either the sub-optimal image quality has to be accepted or the measurement has to be repeated, wherein it can also happen that several recordings have to be repeated in order to re-create the spatial correlation of the various layer orientations. Overall this either leads to limited possible diagnoses by the doctor owing to the poorer image quality, or the MR system is blocked by a person being examined for longer than necessary.

SUMMARY OF INVENTION

Starting from the above-mentioned drawbacks it is an object of the present invention to optimize recording of image data and monitoring of the person being examined as the image data is being recorded such that certain errors in recording of image data are discovered immediately, or such that the cause of the poor image quality can be identified subsequently.

These objects are achieved by the features of the independent claims. Preferred embodiments of the invention are described in the dependent claims.

According to a first aspect of the invention it relates to a method for monitoring recording of measurement data of a person being examined who is positioned on a couch in medical diagnostic equipment. In a first step of the method according to the invention measurement data is recorded by the medical diagnostic equipment to create image data. The pressure characteristic which is exerted on the couch by the person being examined is also detected. The detected pressure characteristic is then automatically analyzed by comparing the pressure characteristic with a predetermined pressure characteristic. The operator of the medical diagnostic equipment is informed if the analyzed pressure characteristic does not match the predetermined pressure characteristic. According to the invention the operator is immediately made aware of certain sources of error during measurement. The cause of error can be isolated because, by way of example, movements by the person being examined can be ruled out in the case of poor image quality if a movement of the person being examined was not detected by the change in pressure. According to the invention the patient's movement can be easily monitored via the change in pressure.

In one embodiment of the invention the pressure characteristic can be detected using a pressure pad which is placed under the person being examined. Due to the fact that the person being examined lies on the pad and compresses it, his movement can be monitored via a change in pressure in the pad. In a further embodiment the pressure characteristic can also be detected by one or more pressure sensor(s) which are integrated directly in the couch on which the person being examined is lying.

In order to subsequently be able to follow a potential movement by a person being examined or patient better, it is possible to store the detected pressure characteristic together with the compiled image data. In this connection the pressure characteristic over time can be stored together with an image which is produced during recording of measurement data for this image. It is also possible to store the pressure characteristic together with the image data only in the event that the pressure characteristic does not match the predetermined pressure characteristic.

The predetermined pressure characteristic, which is used for comparison, can take place by analyzing the previously detected pressure characteristic. This can mean that the pressure characteristic throughout the entire period during which the person being examined is lying on the couch is monitored and stored in order to determine the predetermined pressure characteristic from the previous characteristic (for example by averaging). A change in pressure can occur, for example on breathing, without a movement by the patient, depending on where the pressure sensor is positioned. This change in pressure must accordingly be distinguished from changes in pressure that result due to movement.

The previous pressure characteristic can be analyzed and examined for irregularities. The operator can be informed if excessive variations in the pressure curve point to a movement. If automatic analysis of the pressure characteristic detects an irregularity therein the operator can be informed visually and/or acoustically about this irregularity. Graphical highlighting paired with an acoustic signal is conceivable by way of example.

It is possible for example to infer an irregularity if the current pressure characteristic differs from the previous pressure characteristic by a predetermined value. It is also possible to analyze the gradient of the pressure characteristic, it being possible to infer an irregularity in the pressure characteristic if the increase in pressure or drop in pressure is greater than a predetermined value or is greater than in the predetermined pressure characteristic that was averaged from the previous pressure characteristic.

According to one embodiment a check is made as to whether recording of the measurement data has been started, the pressure characteristic detected during recording of the measurement data being stored in conjunction with the image data. The pressure characteristic that was recorded outside of the period for recording image data can also be stored together with the recording instant. Overall the data can be stored such that at a later instant it is possible to allocate in terms of time measurements that have taken place and measuring breaks.

If an irregularity has been detected in the pressure characteristic an indication of the manner of the irregularity can be displayed and stored with the image data. Along with the indication of the manner of the irregularity, an operator's note on the displayed indication can also be stored with the image data. It is therefore possible for the user to annotate movement reports, it being possible to also pre-configure notes that occur frequently and to assign them to a movement simply by clicking on them. One exemplary note of this kind could be:

The patient only raised his arm but did not change the position of his body

The patient moved a lot and changed the position of his body, etc.

Obviously other self-composed notes can also be input and stored together with the images. If an irregularity has been detected in the pressure characteristic it can be displayed using an operator's visual marking. For example the irregularity can be visually highlighted in the pressure characteristic, whether it is by inserting a frame in the pressure characteristic or by marking the pressure characteristic itself. The medical diagnostic equipment can also be constructed in such a way that when movements are detected the image data generated during the movement is automatically displayed once measurement data acquisition has finished, so the user can check whether the image quality has been affected by the movement.

The invention also relates to medical diagnostic equipment comprising an image creation unit for generating the image data of the person being examined, and a pressure detector which detects the pressure characteristic that the person being examined exerts on the couch. A pressure processing unit examines the pressure characteristic for irregularities and an information unit informs the operator of the diagnostic equipment of the irregularity that has occurred. The pressure detector can, as mentioned above, be a pressure pad or a pressure sensor that is integrated in the couch. Other types of pressure detection are of course also possible.

The invention also relates to a computer program product comprising a computer program which executes the above-described method when run in a computer system, and to an electronically readable storage medium comprising control information which can also execute the above-described method.

BRIEF DESCRIPTION OF THE DRAWINGS

The invention will be described in more detail hereinafter with reference to the accompanying drawings.

DETAILED DESCRIPTION OF INVENTION

Figure 1:
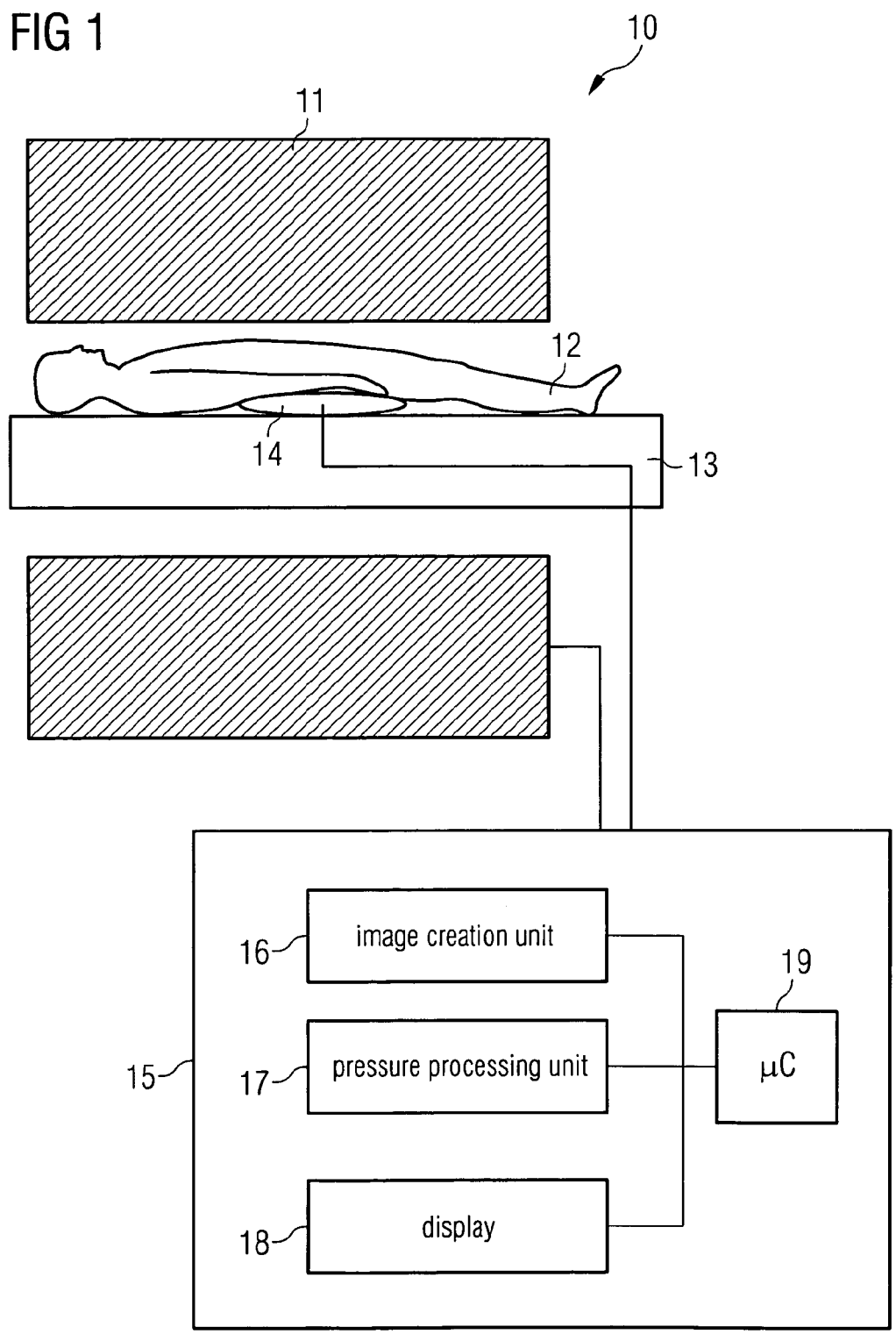
FIG. 1 schematically shows an MR system comprising inventive monitoring of movement.

FIG. 1 schematically shows an MR system 10. This system has a magnet 11 for generating a polarization field B0, this polarization field generating a resultant magnetization in a person being examined 12 which is brought out of the state of equilibrium by an HF (high frequency) system (not shown), relaxation of the magnetization in the state of equilibrium being detected by coils (not shown). Gradient coils (not shown) are also provided for spatial resolution of the detected magnetization and generate a linear magnetic field gradient beyond the polarization field B0. The person being examined 12 shown in FIG. 1 is lying on a couch 13, a pressure sensor 14 in the form of a pressure pad being arranged between the couch 13 and the person being examined 12. Due to the fact that the person being examined is lying on the pad and compresses it, patient movement can be monitored via a change in pressure in the pad.

The pressure sensor, like the MR system itself, is connected to a central control unit 15. This central control unit 15 has an image creation unit 16 with which the imaging parameters for generating the MR images can be determined and with which MR images can be reconstructed from the detected measurement data. A pressure processing unit 17 is also provided which analyzes the pressure characteristic detected by the pressure sensor 14, as will be described in more detail hereinafter with reference to FIGS. 2 to 9. The MR images and the pressure characteristic can be displayed on a display 18. A central processing unit 19 controls the activity and interaction of the various units provided in the central control unit 15, as is sufficiently known to a person skilled in the art of MR systems. The mode of operation of an MR system with the radiation of a sequence of HF pulses and switching of gradients to produce MR images is generally known to a person skilled in the art, so a more precise description thereof will be omitted. In the present case only the aspects important to the understanding of the invention will be discussed.

Figure 2:
FIG. 2 shows a normal pressure curve in bodily regions with a slight breathing influence.
Figure 3:
FIG. 3 shows a normal pressure curve in bodily regions with a greater breathing influence than in FIG. 2.
Figure 4:
FIG. 4 shows a pressure curve in bodily regions with a slight breathing influence with breathing command.
Figure 5:
FIG. 5 shows a normal pressure curve in bodily regions with greater breathing influence and breathing command.

FIG. 2 shows a pressure characteristic 20 with a slight influence during normal breathing, as is detected for example by the pressure sensor 14, if this is arranged in a region below the person being examined 12 that does not correspond with the upper body, in which the pressure differences are most noticeable in the breathing. The slight breathing influence can be seen from the slight elevations 21. FIG. 2 shows a similar pressure characteristic 21 with a greater breathing influence, and this can be seen from the increased elevations 23. Some MR measurements are recorded using the breath-hold technique, and this means that the person being examined should not breathe during recording of the measurement data. In these cases the person being examined is given a breathing command—to hold his breath—by the person operating the MR system. FIGS. 4 and 5 accordingly show pressure characteristics 24 and 25 with breathing command, it being possible to see a slight breathing influence in the pressure characteristic 24 in FIG. 4, while the breathing influence is greater in the pressure characteristic 25 in FIG. 5.

Figure 6:
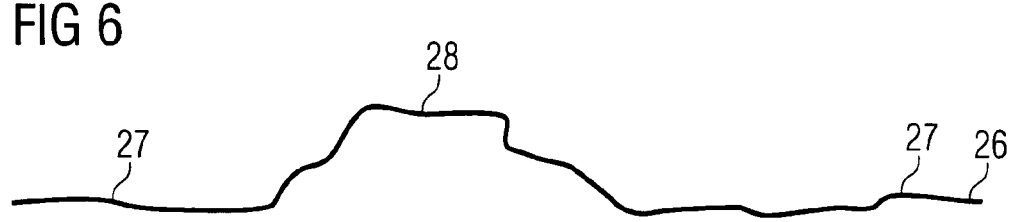
FIG. 6 shows a detail of a pressure curve with patient movement.

The pressure characteristic is accordingly preferably recorded throughout the entire period during which the person being examined is lying on the couch, and a predetermined pressure characteristic is determined from the previous pressure characteristic. The pressure processing unit can analyze the detected pressure characteristics and the user can be informed by way of the displays if excessive variations in the pressure characteristic relative to the previous characteristic point to a movement. FIG. 6 accordingly shows this kind of pressure characteristic 26. The elevations 27 that result from normal breathing clearly differ from elevation 28. If an irregularity such as elevation 28 is detected in the pressure characteristic, the operator can be informed of it visually and/or acoustically. The operator can then accurately assess whether the poor image quality or the spatial difference of various layer orientations were caused by the person being examined moving or not. Analysis in the event of image quality problems, which can be caused by the person being examined, is therefore facilitated and the operator can document that diagnosis of the images was limited owing to a patient-induced reduction in image quality and can consequently comply with his obligation to prove why the data cannot be optimally assessed.

Figure 7:
FIG. 7 shows a normal pressure curve with tolerance range in the bodily regions with a slight breathing influence with normal breathing.
Figure 8:
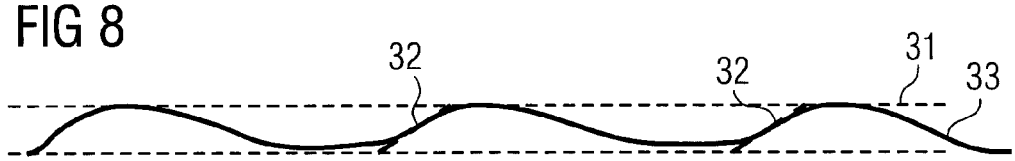
FIG. 8 shows a normal pressure curve with tolerance range in a bodily region with greater breathing influence with breathing command.
Figure 9:
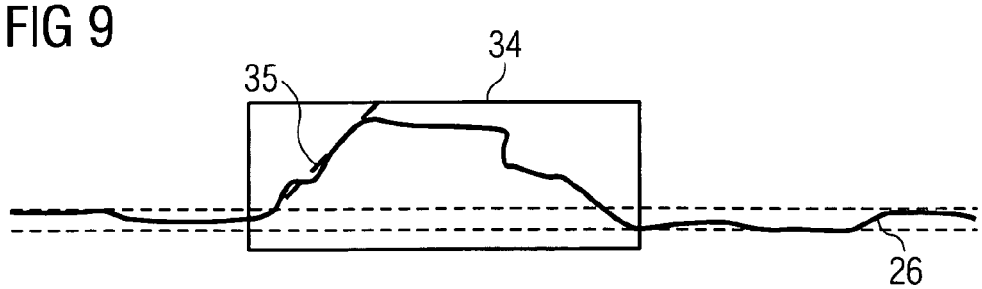
FIG. 9 shows the pressure characteristic of FIG. 6 with patient movement display.

An irregularity in the pressure characteristic can be detected in various ways. As FIGS. 7 and 8 show, it is possible to examine the pressure curve and to define a tolerance window 29 in which the pressure curve normally resides. This tolerance window 29, illustrated by the broken lines in FIGS. 7 to 9, can for example be set at +/−50% of the previous curve height, starting from an initial value, although the operator can also define any other tolerance window. This tolerance window can be calculated if the person being examined lies on the couch for a period, for example between five and 15 seconds, and does not move. FIG. 7 shows a pressure curve 30, which, with a slight breathing influence, runs in tolerance window 29. FIG. 8 shows a tolerance window 31 which was calculated in the case of an intensified breathing influence. The slopes 32 in the breathing curve 33 result from the operator's breathing command. A movement can accordingly be detected for example if pressure values occur in the pressure curve which either lie outside of the tolerance window or differ from the predetermined pressure characteristic by a predetermined value. It can still or also be possible to draw conclusions about the changes in movement via the gradient of the pressure curve. FIG. 9 shows the pressure characteristic 26 of FIG. 6 with the irregularity, it being possible to highlight the irregularity on the display for an operator, for example by a frame 34. The irregularity can be detected via the gradient 35 of the pressure curve and/or via the occurrence of pressure values outside of the tolerance range. The central processor unit 19 can detect whether an MR measurement is being carried out or not, it being possible to store the pressure characteristics that are captured during a measurement together with the image data. The pressure characteristic can then be shown separately or together with the image data. All other measurement data of the pressure characteristic, or even just that during which a movement took place, which was captured outside of the measuring periods can also be stored together and if desired, examined together. The pressure characteristics can be stored in such a way that at a later instant it is possible to allocate in terms of time measurements that have taken place and measuring breaks. If the operator is informed about a movement he can react for example and ask the person being examined whether they moved or whether they are having difficulties lying down and possibly ask him to lie still. It is also possible for the operator to make notes on these movement reports, it being possible for frequently occurring notes to also be pre-configured and to allocate them to the event simply by clicking on them. Further notes can also be subsequently allocated to an event (i.e. a movement). If the person being examined has moved a lot and the position of his body has changed, the spatial allocation of the layer orientation will no longer match up during subsequent recordings. This fact can be subsequently added to an original note and be stored together with the images. If a movement occurred during the measurement the operator will also be made aware of this immediately after the measurement and this indication is automatically stored with the image data and displayed therewith. Further notes such as Measurement was not repeated as data could be diagnosed
Measurement was not repeated as the patient could not tolerate additional measurements can also be preconfigured and stored together with the image data. If the operator should find that the indication is irrelevant it can be removed and on subsequent examination the image data appears without an indication of the irregularity.

It is also possible for the operator to mark movements in the pressure characteristic himself and to activate or deactivate an acoustic signal to illustrate movements. It is also possible to show a timeline which includes the measuring breaks and the measurements as well as the markers for the movements. When displaying the pressure characteristic which occurred during a measurement it is also possible for the corresponding image data to also automatically be displayed.

To summarize, the present invention allows more effective error analysis as to whether the person being examined moved or not.

The invention claimed is:

1. A method for monitoring recording of measurement data of a person being examined and is positioned on a couch in medical diagnostic equipment, comprising:
    recording the measurement data to create image data;
    detecting the pressure characteristic exerted on the couch by the person being examined;
    automatically analyzing the pressure characteristic by comparing the detected characteristic with a predetermined pressure characteristic;
    determining a movement of the person along the couch based on the comparing of the detected pressure characteristic with the predetermined pressure characteristic, said comparing including distinguishing the pressure characteristic associated with the movement of the person along the couch from a pressure characteristic associated with a breathing of the person on the couch;
    informing an operator of the medical diagnostic equipment if the analyzed pressure characteristic does not match the predetermined pressure characteristic;
    wherein the pressure characteristic is detected using a pressure pad arranged at least partially between the person being examined and the couch;
    wherein the pressure characteristic is detected by at least one pressure sensor in the couch;

and wherein the predetermined pressure characteristic is determined by analyzing an immediately previously detected pressure characteristic.

2. The method as claimed in claim 1, wherein the detected pressure characteristic is stored together with the compiled image data.

3. The method as claimed in claim 1 wherein the pressure characteristic is stored together with the image data which was detected during recording of the measurement data.

4. The method as claimed in claim 1, wherein the pressure characteristic is stored together with the image data in which the pressure characteristic does not match the predetermined pressure characteristic.

5. The method as claimed in claim 1, wherein the pressure characteristic is detected substantially throughout the entire period during which the person being examined is lying on the couch.

6. The method as claimed in claim 5, wherein the pressure characteristic being automatically analyzed is examined for irregularities.

7. The method as claimed in claim 6, wherein that on detection of an irregularity in the pressure characteristic the operator of the diagnostic equipment is visually and/or acoustically informed thereof.

8. The method as claimed in claim 7, wherein an irregularity is detected if the current pressure characteristic differs from the previous pressure characteristic by a predetermined value.

9. The method as claimed in claim 8, wherein a gradient of the pressure characteristic is examined and an irregularity is detected if the increase in pressure or the drop in pressure is greater than a predetermined value.

10. The method as claimed in claim 9, wherein a check is made as to whether recording of the measurement data has been started and the pressure characteristic is recorded during recording of the measurement data being stored in conjunction with the image data.

11. The method as claimed in claim 10, wherein the pressure characteristic which was recorded outside of a period for recording the measurement data is stored with the respective recording instant.

12. The method as claimed in claim 11, wherein when an irregularity is detected in the pressure characteristic, an indication of the manner of the irregularity is displayed and is stored with the image data.

13. The method as claimed in claim 12, wherein when displaying the indication of the manner of the irregularity an operator's note on the displayed indication is stored with the image data.

14. The method as claimed in claim 13, wherein when an irregularity is detected, the irregularity is displayed to the operator by visual marking of the irregularity in the pressure characteristic.

15. The method as claimed in claim 14, wherein a deviation from the predetermined pressure characteristic is marked when displaying the pressure characteristic.

16. The method as claimed in claim 15, wherein the image data is displayed in which a deviation from the predetermined pressure characteristic was detected during recording.

17. Medical diagnostic equipment, comprising:
a couch that supports a person being examined;
an image creation unit for producing image data of the person being examined;
a pressure detector that detects a pressure characteristic which the person being examined exerts on the couch;
a pressure processing unit that examines the pressure characteristic for an irregularity in the pressure characteristic as indicative of a movement of the person along the couch, said pressure processing unit to compare the pressure characteristic with a predetermined pressure characteristic, said comparison to distinguish the pressure characteristic associated with the movement of the person along the couch from a pressure characteristic associated with a breathing of the person on the couch;
an information unit that informs an operator of the medical diagnostic equipment about the irregularity;
wherein the pressure characteristic is detected using a pressure pad arranged at least partially between the person being examined and the couch;
wherein the pressure characteristic is detected by at least one pressure sensor in the couch;
and wherein the predetermined pressure characteristic is determined by analyzing an immediately previously detected pressure characteristic.

* * * * *